(12) United States Patent
Wilk

(10) Patent No.: US 7,963,941 B2
(45) Date of Patent: Jun. 21, 2011

(54) INTRA-ABDOMINAL MEDICAL METHOD AND ASSOCIATED DEVICE

(76) Inventor: Peter J. Wilk, New York, NY (US)

(*) Notice: Subject to any disclaimer, the term of this patent is extended or adjusted under 35 U.S.C. 154(b) by 1100 days.

(21) Appl. No.: 11/386,380

(22) Filed: Mar. 22, 2006

(65) Prior Publication Data

US 2006/0229653 A1 Oct. 12, 2006

Related U.S. Application Data

(60) Provisional application No. 60/670,514, filed on Apr. 12, 2005.

(51) Int. Cl.
*A61M 29/00* (2006.01)
(52) U.S. Cl. ............ 604/101.01; 600/104; 604/28; 606/185
(58) Field of Classification Search ............ 600/101, 600/104, 106, 114–116, 121, 153, 156, 158, 600/461–464, 466, 470–471; 604/22, 26, 604/27, 43–45, 101.01–101.05, 506–509, 604/28; 606/185
See application file for complete search history.

(56) References Cited

U.S. PATENT DOCUMENTS

| | | | |
|---|---|---|---|
| 3,253,594 A | 5/1966 | Matthews et al. | |
| 3,730,645 A | 5/1973 | Mashakaru et al. | |
| 4,646,722 A * | 3/1987 | Silverstein et al. | 600/104 |
| 5,209,721 A | 5/1993 | Wilk | |
| 5,242,398 A * | 9/1993 | Knoll et al. | 604/103.05 |
| 5,261,889 A * | 11/1993 | Laine et al. | 604/164.11 |
| 5,297,536 A | 3/1994 | Wilk | |
| 5,458,131 A | 10/1995 | Wilk | |
| 5,458,583 A * | 10/1995 | McNeely et al. | 604/103.13 |
| 5,480,410 A | 1/1996 | Cuschieri et al. | |
| 5,503,616 A | 4/1996 | Jones | |
| 5,545,179 A | 8/1996 | Williamson, IV | |
| 5,634,937 A * | 6/1997 | Mollenauer et al. | 606/213 |
| 5,797,960 A * | 8/1998 | Stevens et al. | 606/213 |
| 5,810,721 A | 9/1998 | Mueller et al. | |
| 5,823,956 A * | 10/1998 | Roth et al. | 600/374 |
| 5,829,447 A * | 11/1998 | Stevens et al. | 128/898 |
| 5,855,614 A * | 1/1999 | Stevens et al. | 128/898 |
| 5,906,577 A | 5/1999 | Beane et al. | |
| 5,924,424 A * | 7/1999 | Stevens et al. | 128/898 |
| 6,079,414 A * | 6/2000 | Roth | 128/898 |
| 6,156,006 A * | 12/2000 | Brosens et al. | 604/104 |

(Continued)

*Primary Examiner* — Thomas J Sweet
*Assistant Examiner* — Samuel Candler
(74) *Attorney, Agent, or Firm* — R. Neli Sudol; Henry D. Coleman; William J. Sapone

(57) ABSTRACT

In a surgical method, a hollow needle is inserted into a hollow internal organ of a patient through a natural body opening. A wireless scanning apparatus is operated externally of the patient to obtain data as to internal structures of the patient on a side of a wall of the organ opposite the body cavity. A distal tip or free end of the needle is passed through the wall of the organ only upon detecting, via the wireless scanning apparatus, an absence of internal organic tissues of the patient in contact with the wall of the organ on the side of the organ opposite the body cavity. Upon the passing of the distal tip or free end of the needle through the wall of the organ, pressurized $CO_2$ gas is conveyed through the needle into the patient on the side of the wall opposite the body cavity. The needle may be connected to the distal end of an elongate flexible hollow shaft and an endoscope may be optionally used to view the needle deployment procedure.

11 Claims, 2 Drawing Sheets

U.S. PATENT DOCUMENTS

| | | |
|---|---|---|
| 6,245,076 B1 | 6/2001 | Yan |
| 6,293,952 B1 * | 9/2001 | Brosens et al. ............... 606/119 |
| 6,346,074 B1 * | 2/2002 | Roth ............................. 600/121 |
| 6,401,720 B1 * | 6/2002 | Stevens et al. ................ 128/898 |
| 6,464,665 B1 * | 10/2002 | Heuser ........................... 604/104 |
| 6,651,672 B2 * | 11/2003 | Roth ............................. 128/898 |
| 6,679,268 B2 * | 1/2004 | Stevens et al. ................ 128/898 |
| 6,692,458 B2 * | 2/2004 | Forman et al. .............. 604/93.01 |
| 6,955,175 B2 * | 10/2005 | Stevens et al. ................ 128/898 |
| 7,100,614 B2 * | 9/2006 | Stevens et al. ................ 128/898 |
| 7,803,195 B2 * | 9/2010 | Levy et al. .................. 623/23.68 |
| 2001/0049497 A1 | 12/2001 | Kalloo et al. |
| 2002/0026094 A1 * | 2/2002 | Roth ............................. 600/121 |
| 2002/0026209 A1 * | 2/2002 | Hung ............................. 606/192 |
| 2002/0096183 A1 * | 7/2002 | Stevens et al. ................ 128/898 |
| 2002/0100485 A1 * | 8/2002 | Stevens et al. ................ 128/898 |
| 2003/0216776 A1 | 11/2003 | Mollenauer et al. |
| 2003/0225402 A1 * | 12/2003 | Stevens et al. .................. 606/39 |
| 2003/0233065 A1 * | 12/2003 | Steward et al. ................. 604/22 |
| 2004/0019348 A1 * | 1/2004 | Stevens et al. .................. 606/34 |
| 2004/0097788 A1 * | 5/2004 | Mourlas et al. ................ 600/116 |
| 2004/0221853 A1 * | 11/2004 | Miller ...................... 128/207.14 |
| 2004/0230160 A1 * | 11/2004 | Blanco ..................... 604/167.06 |
| 2004/0267191 A1 * | 12/2004 | Gifford et al. .................. 604/22 |
| 2005/0101837 A1 * | 5/2005 | Kalloo et al. ................. 600/115 |
| 2005/0107664 A1 * | 5/2005 | Kalloo et al. ................. 600/115 |

* cited by examiner

INTRA-ABDOMINAL MEDICAL METHOD AND ASSOCIATED DEVICE

CROSS-REFERENCE TO RELATED APPLICATION

This application claims the benefit of U.S. Provisional Patent Application No. 60/670,514 filed Apr. 12, 2005.

BACKGROUND OF THE INVENTION

This invention relates to medical procedures carried out without the formation of an incision in a skin surface of the patient.

Such procedures are described in U.S. Pat. Nos. 5,297,536 and 5,458,131.

As described in those patents, a method for use in intra-abdominal surgery comprises the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

Visual feedback may be obtained as to position of a distal end of the incising instrument prior to the manipulating thereof to form the perforation. That visual feedback may be obtained via the endoscope or, alternatively, via radiographic or X-ray equipment.

The abdominal cavity may be insufflated prior to the insertion of the distal end of the endoscope into the abdominal cavity. Insufflation may be implemented via a Veress needle inserted through the abdominal wall or through another perforation in the internal wall of the natural body cavity. That other perforation is formed by the Veress needle itself. U.S. Pat. No. 5,209,721 discloses a Veress needle that utilizes ultrasound to detect the presence of an organ along an inner surface of the abdominal wall.

A method in accordance with the disclosures of U.S. Pat. Nos. 5,297,536 and 5,458,131 comprises the steps of (i) inserting an endoscope through a natural body opening into a natural body cavity of a patient, (ii) inserting an endoscopic type incising instrument through the natural body opening into the natural body cavity, (iii) manipulating the incising instrument from outside the patient to form a perforation in an internal wall of the natural internal body cavity, (iv) moving a distal end of the endoscope through the perforation, (v) using the endoscope to visually inspect internal body tissues in an abdominal cavity of the patient, (vi) inserting a distal end of an elongate surgical instrument into the abdominal cavity of the patient, (vii) executing a surgical operation on the internal body tissues by manipulating the surgical instrument from outside the patient, (viii) upon completion of the surgical operation, withdrawing the surgical instrument and the endoscope from the abdominal cavity, (ix) closing the perforation, and (x) withdrawing the endoscope from the natural body cavity.

The surgical procedures of U.S. Pat. Nos. 5,297,536 and 5,458,131 reduce trauma to the individual even more than laparoscopic procedures. Hospital convalescence stays are even shorter.

OBJECTS OF THE INVENTION

It is an object of the present invention to provide improvements on the afore-described surgical procedures.

It is another object of the present invention to provide a method and/or an associated device for use particularly in the insufflation portion of the procedures.

These and other objects of the present invention will be apparent from the drawings and detailed descriptions herein. While every object of the invention is believed to be attained in at least one embodiment of the invention, there is not necessarily any single embodiment that achieves all of the objects of the invention.

SUMMARY OF THE INVENTION

A surgical method in accordance with the present invention comprises inserting a hollow needle into a hollow internal organ of a patient, the organ communicating with the ambient environment via a natural body opening, the organ defining an internal body cavity. The needle is inserted into the organ through the natural body opening. The method further comprises (a) operating a wireless scanning apparatus externally of the patient to obtain data as to internal structures of the patient on a side of a wall of the organ opposite the body cavity and (b) passing a distal tip or free end of the needle through the wall of the organ only upon detecting, via the wireless scanning apparatus, an absence of internal organic tissues of the patient in contact with the wall of the organ on the side of the organ opposite the body cavity. Upon the passing of the distal tip or free end of the needle through the wall of the organ, a pressurized fluid is conveyed through the needle into the patient on the side of the wall opposite the body cavity. The pressurized fluid is typically carbon dioxide gas.

The wireless scanning apparatus may utilize any type of waveform energy suitable for obtaining image data of structures internal to a patient's body. Thus, the wireless scanning apparatus may take the form of a magnetic resonance imaging apparatus, an X-ray machine, a CAT scanner, or an ultrasound apparatus. In the case of an ultrasound apparatus, the method additionally comprises transmitting ultrasonic pressure waves into the patient and sensing echo waveforms reflected from internal tissues of the patient.

The needle may be located at a distal end of an elongate flexible shaft member. In that event, the method additionally comprises inserting the needle into the patient along a non-linear path having at least one bend or turn. A distal end portion of an endoscope insertion member may be inserted into the hollow internal organ and used to view the wall of the hollow internal organ from the body cavity. Where the endoscope has a sheath with a longitudinally extending channel, the needle may be inserted into the body cavity via the channel.

Pursuant to an optional feature of the present invention, the method also comprises inserting a distal end portion of an endoscope insertion member into the hollow internal organ and using the endoscope to view the wall of the hollow internal organ from the body cavity.

Pursuant to another feature of the present invention, the passing of the distal tip or free end of the needle through the organ wall results in a perforation in the wall. The method may further comprise removing the needle from the wall, inserting a port element in a collapsed configuration into the body cavity, deploying the port element in the organ wall so that parts of the port element are disposed on opposing sides of the wall, and after the deploying of the port element, expanding the parts of the port element into expanded configurations so that the wall is sandwiched between the expanded port element parts.

A surgical method comprises, in accordance with a particular embodiment of the present invention, inserting a hollow needle into a hollow internal organ of a patient, where the organ communicates with the ambient environment via a natural body opening and the organ defines an internal body cavity, the needle being inserted into the organ through the natural body opening and the needle being located at a distal end of an elongate flexible shaft member. The inserting of the needle into the patient includes passing the needle and a distal end portion of the shaft member along a nonlinear path having at least one bend or turn. A distal or free end of the needle is inserted through a wall of the organ and thereafter a pressurized fluid is conveyed through the needle into the patient on the side of the wall opposite the body cavity.

The method may further comprise inserting a distal end portion of an endoscope insertion member into the hollow internal organ and using the endoscope to view the wall of the hollow internal organ from the body cavity. Where the endoscope has a sheath with a longitudinally extending channel, the needle may be inserted into the body cavity via the channel. Typically, the needle is housed in a delivery tube that is inserted through the channel in the endoscope sheath. The distal end of the tube thus serves as a shield preventing the needle from penetrating and perforating the wall of the channel.

Alternatively, instead of being inserted through the sheath channel after the deployment of the endoscope insertion member inside the hollow internal organ of the patient, the needle instrument may be stored inside the channel at manufacture and inserted together with the endoscope into the internal organ through the natural body opening. The distal end portion of the channel may be provided with a liner of a smooth hard material to encapsulate and isolate the needle during the insertion procedure, thereby protecting the soft tissues of the natural body opening during the deployment procedure.

Where the passing of the distal tip or free end of the needle through the organ wall results in a perforation in the wall, the method of this embodiment may further comprise removing the needle from the wall, inserting a port element in a collapsed configuration into the body cavity, deploying the port element in the organ wall so that parts of the port element are disposed on opposing sides of the wall, and after the deploying of the port element, expanding the parts of the port element into expanded configurations so that the wall is sandwiched between the expanded port element parts.

A surgical device in accordance with the present invention comprises an elongate flexible hollow shaft or tube, a hollow needle connected to one end of the shaft or tube, and a coupling element at an opposite end of the shaft or tube for operatively connecting the shaft or tube and concomitantly the needle to a source of pressurized carbon dioxide gas. The shaft or tube may be insertable though a working channel associated with a flexible endoscope.

A surgical kit comprises, in accordance with the present invention, a surgical instrument having an elongate flexible hollow shaft and a hollow needle disposed at a distal end of the shaft. The kit further comprises a port element with parts disposable on opposite sides of a body organ wall, the port element having an aperture enabling passage of a distal end portion of an elongate medical instrument into a body cavity through the body organ wall.

The port element may have a collapsed insertion configuration and an expanded use configuration.

The surgical kit may additionally comprise the medical instrument, where the medical instrument has an elongate flexible shaft and an operative tip at a distal end thereof, the operative tip being different from a needle.

The shaft may be adapted for insertion though a working channel associated with a flexible endoscope, i.e., a biopsy channel provided in the endoscope insertion shaft or a working channel in an endoscope sheath used with the endoscope.

The shaft of the needle instrument is preferably provided at a proximal end with a coupling element for operatively connecting the shaft and concomitantly the needle to a source of pressurized carbon dioxide gas.

DETAILED DESCRIPTION

Figure 1:
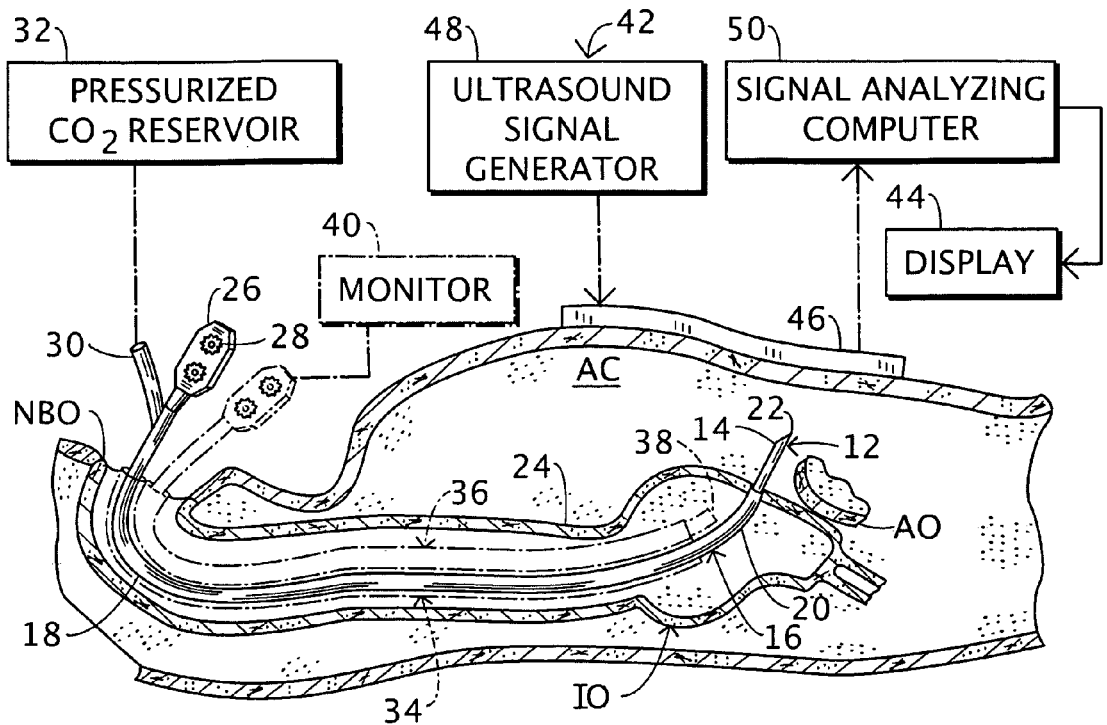
FIG. 1 is a schematic partial longitudinal cross-section of a human patient, showing an abdomen-insufflation step in a trans-organ surgical procedure in accordance with the present invention.

As illustrated in FIG. 1, a method for insufflating a patient's abdominal cavity AC during a trans-organ surgical procedure as described in U.S. Pat. Nos. 5,297,536 and 5,458,131 (both incorporated by reference herein) includes inserting a distal end portion of an insufflation instrument 12 into a hollow internal organ IO of the patient via a natural body opening NBO of the patient. Internal organ IO, which defines an internal body cavity IC, may be the stomach, the urinary bladder, the colon, or the vagina, while the natural body opening NBO is the mouth, the urethral orifice, the anus, or the vaginal orifice.

Instrument 12 includes a hollow needle 14 at a distal end of a tubular flexible shaft member 16. The inserting of needle 14 into the patient may include passing the needle and a distal end portion of the shaft member 16 along a nonlinear path (not separately designated) having at least one bend or turn 18, 20. A distal or free end 22 of needle 14 is inserted through a wall 24 of the organ IO and thereafter a pressurized fluid is conveyed through shaft 16 and needle 14 into the patient's abdominal cavity AC on the side of wall 24 opposite the internal body cavity IC.

Shaft 16 may be coupled at a proximal end to a handpiece 26 provided with one or more steering control or actuator knobs 28 and a port 30 connected to a source 32 of pressurized carbon dioxide gas.

Needle 14 and the distal end portion of shaft 16 may be inserted into the patient and particularly into organ IO through a tubular working channel 34 of an endoscope sheath 36. Needle 14 may be disposed inside channel 34 at the time of manufacture and thus inserted into the patient together with an endoscope 38. Endoscope 38 is connected to a video monitor 40 for enabling a surgeon to view the insertion path and the inner surface of wall 24 during the perforation or penetration of the organ wall by needle 14.

If needle 14 is inserted into cavity IC together with endoscope 38 and sheath 36, channel 34 may be formed with an inner lining that is made of a hard, puncture resistant material. Alternatively, needle 14 may be housed in a dedicated deployment tube (not illustrated) that may be inserted into channel 34 after the insertion of endoscope 38 and sheath 36 into the patient.

As an alternative or additional method for the monitoring of organ IO and needle 14 prior to and during the penetration of wall 24 by the needle, a wireless scanning apparatus such as an ultrasound scanner 42 may be used to view internal organ IO and other structures inside the patient on a display or monitor 44. Ultrasound scanner 42 may particularly include a transducer carrier 46 placed in contact with the patient, an ultrasonic waveform generator 48 operatively connected to the carrier for energizing the transducers (e.g., piezoelectric crystals, not shown) thereof, and a computer 50 functioning as an ultrasound signal analyzer operatively connected to the carrier for receiving therefrom signals encoding ultrasonic waves reflected from internal structures.

An entirely electronic (no moving parts) ultrasound scanner suitable for the present purposes is disclosed in the following patents: U.S. Pat. No. 5,871,446, U.S. Pat. No. 6,023,032, U.S. Pat. No. 6,319,201, U.S. Pat. No. 6,106,463, and U.S. Pat. No. 6,306,090. Other kinds of ultrasound scanning devices, as well as magnetic resonance imaging, X-ray machines, and CAT scanners, may also be suitable for present purposes, i.e., for monitoring the shapes and relative positions of organ IO and other internal tissue structures.

Ultrasound scanner 42 is operated and display or monitor 44 viewed in order to determine whether a selected location along organ wall 24 is free and clear of other intra-abdominal organs or whether organ wall 24 at a selected location lies against another organ AO or the patient. This determination is made prior to the penetration of wall 24 by needle 14, to ensure that needle 14 does not enter another organ AO and conduct insufflation fluid into that other organ. Instead, the point of penetration of needle 14 through wall 24 is selected to avoid adjacent organ structures AO, so that needle 14 subsequently conducts carbon dioxide gas into abdominal cavity AC.

Figure 2:
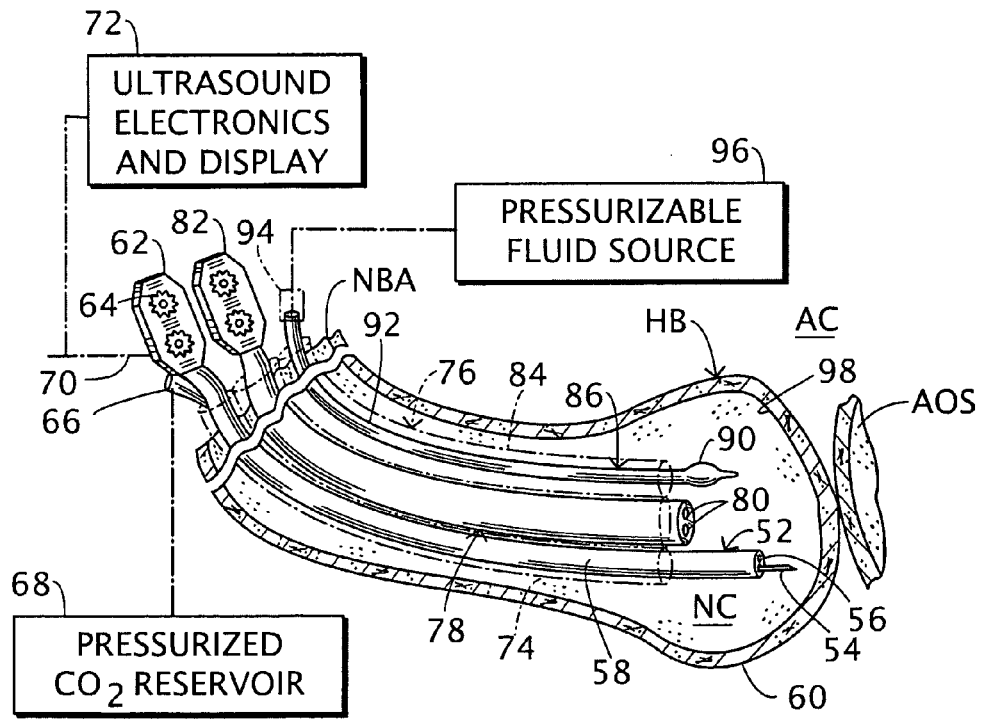
FIG. 2 is a schematic cross-sectional view of a hollow internal organ of a patient, showing a step in a modified abdomen-insufflation step of a trans-organ surgical procedure in accordance with the present invention.

FIG. 2 depicts an alternative abdomen inflation method wherein the detection of an adjacent organ structure AOS inside the patient is accomplished via an ultrasound probe 52 that is inserted into a hollow body organ HB via a natural body opening or aperture NBA together with an insufflation needle 54. Probe 52 may specifically include one or more ultrasound transducers 56 disposed in the end of an elongate flexible tubular member 58 from which needle 54 is ejected into a natural body cavity NC defined by a wall 60 of organ HB. Needle 54 is coupled to the distal end of an elongate flexible tubular shaft (not shown) such as shaft 16 in FIG. 1. Such an elongate flexible tubular shaft is insertable through a lumen or channel inside tubular member 58. That lumen or channel may be lined at a distal end with a layer of a hard low-friction material such as polytetrafluoroethylene, to facilitate the ejection of needle 54.

Probe 52 may include a handpiece 62 connected to a proximal end of tubular member 58, the handpiece being provided with steering controls 64 and a port 66 for coupling to a source or reservoir 68 of pressurized carbon dioxide gas (possibly in liquid form). Handpiece 62 is also provided with a connector 70 for forming an electrically conductive link to an ultrasound electronics apparatus and display 72. This electrically conductive link enables the transmission of ultrasound pressure waves and the sensing of incoming reflected waveforms by 56 under the control of ultrasound electronics apparatus 72.

Probe 52 and needle 54 may be inserted into cavity NC through a collapsible tubular channel element 74 of an endoscope sheath 76 attached to and surrounding an endoscope 78. Endoscope 78 has optical elements 80 and a handpiece 82. Sheath 76 may be provided with a second tubular channel 84 through which an instrument 86 is inserted into cavity NC of organ HB for deploying a port element 88 (FIG. 3B) in organ wall 60. At the time of insertion, instrument 86 includes port element 88 in a collapsed or folded insertion configuration 90 and an elongate flexible tubular shaft 92. At a proximal end, shaft 92 includes a port or connector schematically represented at 94 for coupling the shaft to a source 96 of pressurized fluid such as saline solution.

Figure 3A:
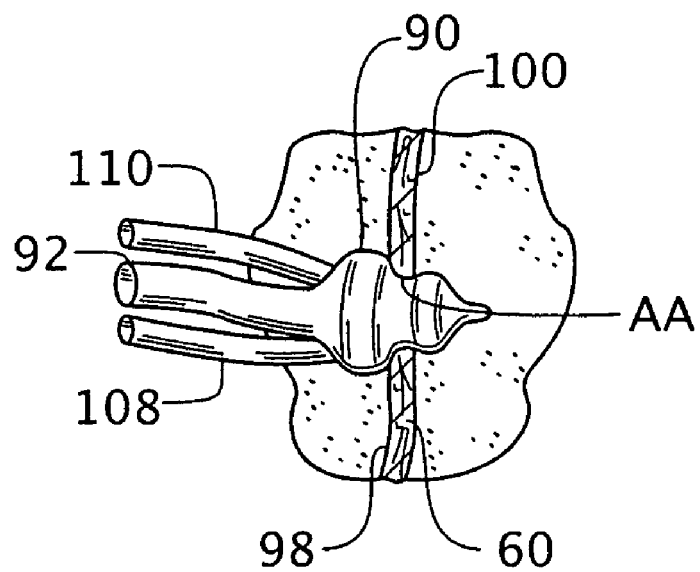
FIG. 3A is a schematic partial cross-sectional view of the organ of FIG. 2, showing a step in the deployment of a trans-organ port.

Upon the insertion of needle 54 and probe 52 into cavity NC of organ HB and the subsequent placement of transducer elements 56 into contact with a proximal surface 98 (FIGS. 3A and 3B) of organ wall 60, ultrasound electronics 72 are operated to scan through the organ wall for the presence of an adjacent organ structure AOS in contact with or proximate to a distal surface 100 (FIGS. 3A and 3B) of wall 60. If an adjacent organ structure AOS is detected, probe 52 is manipulated from outside the patient to reposition the probe head (not separately enumerated) including transducer elements 56 at another location along proximal surface 8 of organ wall 60. Upon failing to detect an adjacent organ structure AOS alongside distal surface 100 of organ wall 60, the operating surgeon moves needle 54 in a distal direction to penetrate through wall 60. Upon completed penetration, carbon dioxide gas from source or reservoir 68 through the flexible shaft or tube (not shown) and into the abdominal cavity AC via needle 54.

Figure 3B:
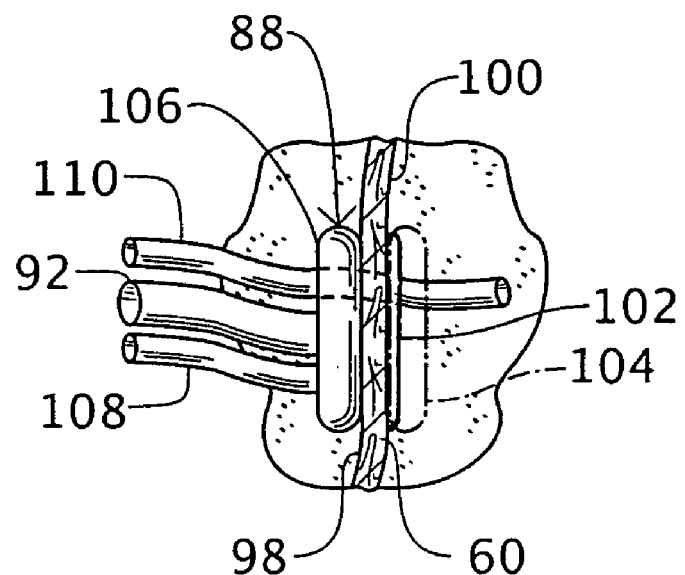
FIG. 3B is a schematic partial cross-sectional view similar to FIG. 3A, showing a subsequent step in the deployment of the trans-organ port of FIG. 3A.

Upon an insufflation of the abdominal cavity by this method, needle 54 is withdrawn from organ wall 60. Then instrument 86 in moved forward so that the collapsed form 90 of port element 88 may be pushed partially through organ wall 60 at the former site of needle penetration (see FIG. 3A). Subsequently, a disk 102 or balloon 104 on the distal side of port element 88 is expanded from the collapsed configuration 90 of the port element, as shown in FIG. 3B, while a balloon or bladder element 106 on the proximal side of the port element is inflated to an expanded configuration.

Disk 102 is made of a flexible sheet material. Disk 102 (or balloon 104) and balloon 106 define respective apertures (not shown) that are aligned with one another to define a hole for the passage of a medical instrument (not shown) through the port element 88. Balloon 106 is attached to disk 102 and has an inflation tube 108 for enabling an introduction of a pressurizing fluid into the balloon to expand the balloon from a collapsed insertion configuration to an inflated use configuration. (In the case of balloon 104 in place of disk 102, balloons 104 and 106 communicate with one another to enable an inflating of both balloons via saline or other fluid conveying through tube 108.)

At least one valve element in the form of a self-sealing membrane or film (not shown) may be provided on port element 88 for forming a seal about the shaft of a medical instrument inserted through the port element into abdominal cavity AC during a trans-organ procedure as described in U.S. Pat. Nos. 5,297,536 and 5,458,131. The valve element or self-sealing membrane may be realized as a resilient annular flange or film material about at least one of the apertures in the disk 102 and the balloon 106.

Another elongate tube 110 may be attached to port element 88, traversing the port element, for the introduction of gas (e.g., carbon dioxide) to maintain pneumoperitoneum in abdominal cavity AC during a trans-organ procedure as described in U.S. Pat. Nos. 5,297,536 and 5,458,131.

Disk 102 may be provided along an edge or periphery with a ring (not shown) of a resilient material stiffer than the flexible sheet material of the disk. The ring assists in spreading disk 102 during a deployment procedure, after a passing of disk 102 in a collapsed form through the artificial aperture AA formed in organ wall 60, for instance, by needle 54 or an incising instrument (not shown). Alternatively, where the ring is omitted, disk 102 is held in an opened configuration by the higher gas pressure in the abdominal cavity AC.

In a trans-organ surgical procedure as described in U.S. Pat. Nos. 5,297,536 and 5,458,131, port element 88 is connected to wall 60 and disposed in artificial aperture AA to keep that aperture open during a surgical procedure conducted via organ HB and natural body cavity NC, as described in U.S. Pat. Nos. 5,297,536 and 5,458,131. Upon completed deployment of port element 88, disk 102 (or balloon 104) and balloon 106 sandwich organ wall 60 and maintain access to abdominal cavity AC via aperture AA.

Port element 88 may be used upon completion of the insufflation operation discussed above with reference to FIG. 1. Needle 54 may be inserted into the patient along a nonlinear path having at least one bend or turn. Alternatively, in some cases, the needle 54 may be inserted into the patient along a linear path.

Insufflation instrument 12, 52, etc., may be marketed as a component of a kit including port element 88 and/or one or more surgical instruments having elongate flexible shafts provided at proximal ends with handle or actuators and at distal ends with operative tips such as scalpel blades, scissors, forceps, cauterizers, retrieval pouches, snares, etc. The instruments of the kit may vary in accordance with different kinds of procedures that may be performed via trans-organ access as described above. Thus, a tubal ligation would require a clip applier. A bladder removal procedure could utilize a cutting and cauterization tool, a graspers and a tissue removal instrument (none shown in particular). The kit may further include sheath 36, which may include more than two working channels should more than one instrument be required simultaneously during a contemplated procedure.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising:
    inserting a hollow needle into a hollow internal organ of a patient, said organ communicating with the ambient environment via a natural body opening, said organ defining an internal body cavity, said needle being inserted into said organ through said natural body opening, said needle being located at a distal end of an elongate flexible shaft member, said shaft member being provided at a proximal end with a handpiece having a steering control or actuator;
    inserting a distal end portion of an endoscope insertion member into said hollow internal organ, said endoscope having a sheath, said endoscope being disposed in a longitudinally extending first tubular channel in said sheath, said sheath being provided with at least one longitudinally extending second tubular channel different from said first tubular channel, said needle being inserted into said body cavity via said second tubular channel;
    thereafter using said endoscope to view a wall of said hollow internal organ from said body cavity;
    inserting a distal or free end of said needle through said wall of said organ;
    upon a passage of said distal or free tip of said needle through said wall of said organ, conveying a pressurized fluid through said needle into the patient on the side of said wall opposite said body cavity in an amount sufficient to insufflate an abdominal cavity of the patient;
    removing said needle from said wall;
    inserting a port element in a collapsed configuration into said body cavity;
    deploying said port element in said organ wall so that parts of said port element are disposed on opposing sides of said wall; and
    after the deploying of said port element, expanding at least a portion of said port element into an expanded configuration so that said wall is sandwiched between expanded port element parts,
    said sheath is provided with at least one longitudinally extending additional tubular channel different from said first tubular channel and said second tubular channel, said a port element being inserted in a collapsed configuration into said body cavity via said additional tubular channel.

2. The method defined in claim 1, further comprising:
    operating a wireless scanning apparatus to obtain data as to internal structures of the patient on a side of said wall of said organ opposite said body cavity,
    the inserting of said distal or free end of said needle through said wall of said organ including passing said distal or free end of said needle through said wall of said organ only upon detecting, via said wireless scanning apparatus, an absence of internal organic tissues of the patient in contact with said wall of said organ on the side of said wall opposite said body cavity.

3. The method defined in claim 2 wherein said needle is located at a distal end of an elongate flexible shaft member, further comprising inserting said needle into the patient along a nonlinear path having at least one bend or turn.

4. The method defined in claim 2 wherein said wireless scanning apparatus is an ultrasound apparatus, further comprising transmitting ultrasonic pressure waves into the patient and sensing echo waveforms reflected from internal tissues of the patient.

5. The method defined in claim 2 wherein said pressurized fluid is carbon dioxide gas.

6. The method defined in claim 1 wherein said pressurized fluid is carbon dioxide gas.

7. A surgical kit comprising:
    a surgical instrument having an elongate flexible hollow shaft, a handpiece provided at a proximal end of said shaft and having at least one steering control or actuator, a hollow needle disposed at a distal end of said shaft and coupling means at said proximal end of said shaft for operatively connecting said shaft and concomitantly said needle to a source of pressurized carbon dioxide gas;
    a port element with parts disposable on opposite sides of a body organ wall, said port element having an aperture enabling passage of a distal end portion of an elongate medical instrument into a body cavity through the body organ wall, said port element having an elongate tube attached to and traversing said port element for the introduction of gas to maintain pneumoperitoneum in a patient's abdominal cavity, said elongate tube being different from said surgical instrument; and a sheath having a plurality of longitudinally extending tubular channels, one of said channels configured for receiving a flexible endoscope shaft, said surgical instrument being insertable through another one of said channels, said port element being insertable in a collapsed insertion configuration through one of said channels.

8. The surgical kit defined in claim 7 wherein said port element has at least said collapsed insertion configuration and an expanded use configuration.

9. The surgical kit defined in claim 7, further comprising said medical instrument, said medical instrument having an elongate flexible shaft and an operative tip at a distal end thereof, said operative tip being different from a needle, said medical instrument being insertable through one of said channels.

10. The surgical kit defined in claim 7 wherein said shaft is insertable though a working channel associated with a flexible endoscope.

11. A surgical method comprising:

inserting a sheath member into a hollow internal organ of a patient, said sheath member having a plurality of longitudinally extending tubular channels different from one another, said organ communicating with the ambient environment via a natural body opening, said organ defining an internal body cavity, said sheath member being inserted into said organ through said natural body opening;

inserting a hollow needle into said hollow internal organ via one of said tubular channels of said sheath member;

passing a distal tip or free end of said needle through said wall of said organ;

upon the passing of the distal tip or free end of said needle through said wall of said organ, conveying a pressurized fluid through said needle into the patient on the side of said wall opposite said body cavity in an amount sufficient to insufflate an abdominal cavity of the patient;

inserting a port element in a collapsed configuration into said hollow internal organ via another of said tubular channels different from said one of said tubular channels;

deploying said port element in said organ wall so that parts of said port element are disposed on opposing sides of said wall; and after the deploying of said port element, expanding at least a portion of said port element so that said wall is sandwiched between the port element parts.

* * * * *